United States Patent [19]

Isogaya et al.

[11] Patent Number: 5,508,303
[45] Date of Patent: Apr. 16, 1996

[54] HAIR-GROWING COMPOSITION

[75] Inventors: Masafumi Isogaya, Kamakura; Shintaro Nishio, Ebina, both of Japan

[73] Assignee: Toray Industries, Inc., Tokyo, Japan

[21] Appl. No.: 68,205

[22] Filed: May 28, 1993

[30]   Foreign Application Priority Data

May 29, 1992   [JP]   Japan ..................................... 4-138187

[51] Int. Cl.$^6$ ........................ A61K 31/34; C07D 307/93
[52] U.S. Cl. ............................................ 514/468; 549/458
[58] Field of Search ............................... 514/468; 549/458

[56] References Cited

U.S. PATENT DOCUMENTS

| | | | |
|---|---|---|---|
| 4,474,802 | 10/1984 | Ohno et al. ............................... | 514/468 |
| 5,280,018 | 1/1994 | Ritter et al. ................................ | 514/63 |

FOREIGN PATENT DOCUMENTS

| | | |
|---|---|---|
| 0060640 | 9/1982 | European Pat. Off. . |
| 0084856 | 8/1983 | European Pat. Off. . |
| 0249194 | 12/1987 | European Pat. Off. . |
| 88/01867 | 3/1988 | WIPO . |

OTHER PUBLICATIONS

Rony et al., *The Journal of Investigative Dermatology*, 21, pp. 313–330 (1953).

Fragrance Journal, 1989 (5), pp. 20–29, (English Translation Included).

Database WPI, Week 3645, Derwent Publications Ltd., AN 86-295722; Daiichi Seiyaku KK, JP61218510, Sep. 29, 1986.

*Primary Examiner*—Richard L. Raymond
*Assistant Examiner*—Deborah Lambkin
*Attorney, Agent, or Firm*—Birch, Stewart, Kolasch & Birch

[57]   ABSTRACT

A composition for stimulating hair growth is described. The composition comprises as an effective ingredient a 5,6,7-trinor-4,8-inter-m-phenylene prostaglandin $I_2$ derivative of the formula (I) or a pharmaceutically acceptable salt thereof.

8 Claims, No Drawings

HAIR-GROWING COMPOSITION

BACKGROUND OF THE INVENTION

I. Field of the Invention

This invention relates to a composition for stimulating growth of hair.

II. Description of the Related Art

Prostaglandin $I_2$ ($PGI_2$, prostacyclin) is a substance known to have strong platelet-aggregation inhibition activity and vasodilating activity. However, since $PGI_2$ to has an unstable exoenol structure, it is extremely unstable even in neutral aqueous solution and is easily converted to 6-oxo-$PGF1\alpha$ which has substantially no activities. The instability of $PGI_2$ is a great problem in using this compound as a pharmaceutical. Furthermore, $PGI_2$ is unstable in the body and its duration of pharmacological activity is short. To eliminate these drawbacks of PGI2, $PGI_2$ derivatives in which the characteristic exoenol ether moiety of $PGI_2$ is converted to inter-m-phenylene have been proposed in, for example, Japanese Laid-open Patent Application (Kokai) Nos. 57-32277, 57-144276 and 58-124778. However, there is no disclosure or suggestion in these and other published references that these $PGI_2$ derivatives have activities to stimulate hair growth and the usefulness for the treatment of alopecia.

SUMMARY OF THE INVENTION

Accordingly, an object of the present invention is to provide a composition for stimulating or promoting hair growth of an animal including human. Another object of the present invention is to provide a method for stimulating or promoting hair growth of an animal including human.

The present inventors intensively studied to find that the $PGI_2$ derivatives have activities to stimulate or promote hair growth of animals including human, thereby completing the present invention.

That is, the present invention provides a hair-growing composition comprising a 5,6,7-trinor-4,8-inter-m-phenylene prostaglandin $I_2$ derivative of the formula (I) below or a pharmaceutically acceptable salt thereof in a pharmaceutically acceptable vehicle in an amount effective for stimulating growth of hair:

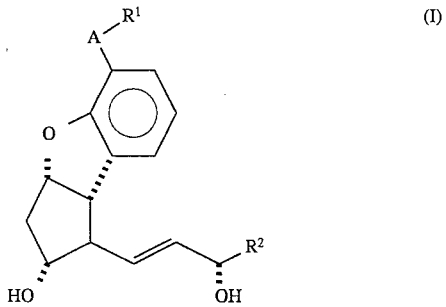

(I)

(wherein $R^1$ represents hydrogen, carboxylic group or a functional derivative thereof, —$CH_2OH$ or a pharmaceutically acceptable cation;

A represents (i) —$(CH_2)_n$—,
(ii) —$(CH_2)_m$—CH=CH—$(CH_2)_p$—,
(iii) —$(CH_2)_m$—C≡C—$(CH_2)_p$— or
(iv) —$CH_2$—O—$CH_2$—

(wherein n represents an integer of 0–3, m and p, the same or different, represent 0 or 1);

$R^2$ represents (i) $C_5$–$C_{10}$ straight or branched alkyl group,
(ii) —$C_tH_{2t}$—$OR^3$ (wherein t represents an integer of 1–5, $R^3$ represents $C_1$–$C_5$ straight or branched alkyl group or phenyl group),
(iii) —$C_tH_{2t}$—CH=C($R^4$)($R^5$)

(wherein t represents the same meaning as mentioned above, $R^4$ and $R^5$, the same or different, represent hydrogen, methyl, ethyl, propyl or butyl group), or (iv) —$C_tH_{2t}$—C≡C—$R^6$ (wherein t represents the same meaning as mentioned above, $R^6$ represents hydrogen, methyl or ethyl group, and —$C_tH_{2t}$ in (ii), (iii) and (iv) represent straight or branched alkylene group);

wherein said compound of the formula (I) may be d-, l- or dl-form.

The present invention also provides a method to promote the hair growth of an animal including human comprising administering to said animal a 5,6,7-trinor-4,8-inter-m-phenylene prostaglandin $I_2$ derivative of the above-described formula (I) or a pharmaceutically acceptable salt thereof in an amount effective for stimulating hair growth of said animal.

The hair-growing composition exhibits high activity to stimulate or promote hair growth in animals including human when orally or parenterally administered.

DETAILED DESCRIPTION OF THE PREFERRED EMBODIMENTS

As described above, the effective ingredient having hair-growing activity in the composition according to the present invention is represented by the above-described formula (I). The functional derivative of carboxylic group for $R^1$ means the derivative of identical function, such as carboxylic esters. The pharmaceutically acceptable cation for $R^1$ may be an alkaline metal or an alkaline earth metal such as sodium, potassium or calcium. The compound represented by the formula (I) may be optically active d-form (d-optical isomer) or l-form (l-optical isomer) or may be racemate (dl-form).

Among the $PGI_2$ derivatives represented by the formula (I), preferred are those represented by the formula (II):

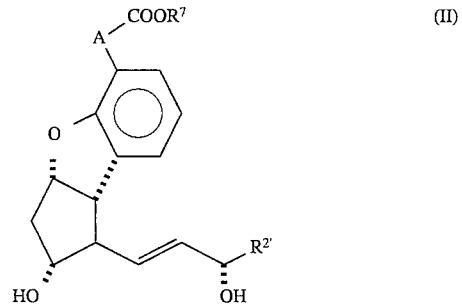

(II)

(wherein $R^7$ represents methyl or ethyl, a pharmaceutically acceptable alkaline metal or alkaline earth metal, or an amine or basic amino acid;

A represents (i) —$(CH_2)_n$—,
(ii) —$(CH_2)_m$—CH=CH—$(CH_2)_p$—,
(iii) —$(CH_2)_m$—C≡C—$(CH_2)_p$— or (iv) —CH$_2$—O—CH$_2$—

(wherein n' represents an integer of 1–3, m and p represent the same meanings as in formula (I));

R$^{2'}$ represents
(i) C$_5$–C$_7$ straight or branched alkyl group,
(ii) —C$_{t'}$H$_{2t'}$—OR$^{3'}$ (wherein t' represents an integer of 1–3, R$^{3'}$ represents C$_2$–C$_4$ straight or branched alkyl group or phenyl group,
(iii) —C$_{t'}$H$_{2t'}$—CH=C(R$^4$) (R$^5$) (wherein t' represents the same meaning as mentioned above, R$^4$ and R$^5$ represent the same meanings as in formula (I)), or
(iv) —C$_{t'}$H$_{2t'}$—C≡C—R$^6$ (wherein t' represents the same meaning as mentioned above, R$^6$ represents the same meaning as in formula (I), and —C$_{t'}$H$_{2t'}$—in (ii), (iii) and (iv) represent straight or branched alkylene group);

wherein said compound of the formula (II) may be d-, l- or dl-form.

In the formula (II), the pharmaceutically acceptable alkaline metal or alkaline earth metal for R$^7$ may preferably be sodium, potassium or calcium. The amine and the basic amino acid for R$^7$ may preferably be one selected from the group consisting of monomethylamine, dimethylamine, trimethylamine, methylpiperidine, monoethanolamine, diethanolamine, triethanolamine and lysine.

As mentioned above, the PGI$_2$ derivatives represented by the formula (I) per se are known and the production processes thereof are described in, for example, U.S. Pat. No. 4,474,802.

The compounds represented by the formula (I) exhibit hair-growing activities when administered orally or parenterally.

The compounds represented by the formula (I) may usually be administered in a dose of 0.01–100 mg/body and 1–3 times a day (i.e., 0.01–300 mg/body/day).

Although the compounds represented by the formula (I) alone can be administered, they can also be administered together with a pharmaceutically acceptable vehicle.

For oral administration, the active compound may be formulated with a pharmaceutically acceptable vehicle to form a solid composition. Preferred examples of the pharmaceutically acceptable vehicle used for this purpose include starches, lactose, sucrose, glucose, mannitol, calcium carbonate, calcium sulfate and the like. The composition may also contain a binding agent such as starch, dextrin, gum arbicae, tragacanth, methyl cellulose, gelatin, polyvinylpyrrolidone, polyvinyl alcohol or the like; a disintegrator such as starch, polyvinylpyrrolidone, crystalline cellulose or the like; a lubricant such as magnesium stearate, talc or the like; a coloring agent; and a perfume.

The formulation for oral administration may be in the form of tablets, sugar-coated tablets, powder, granules, troches, capsules, balls and syrups.

For parenteral administration, the composition may be formulated into an aqueous sterilized solution for injection (subcutaneous, intravenous, intramuscular, intraperitoneal or the like). The solution may contain other solutes such as sodium chloride or glucose in an amount sufficient to make the solution isotonic.

The concentration of the active ingredient in the composition for oral or parenteral administration is not restricted and may usually be 0.1 ng/ml to 500 μg/ml.

Since the compound of the formula (I) has a stable chemical structure, there is no difficulty in formulating the compound. Thus, in addition to the above-described formulations for oral administration and for injection, the compound may easily be formulated in the form of an absorption-promoting agent, a topical formulation such as ointment, and in the form of a suppository.

The present invention will now be described by way of examples thereof. It should be noted that the examples are presented for the illustration purpose only and should not be interpreted in any restrictive way.

EXAMPLE

The compound having a structure shown in Table 1 (beraprost) was tested for its hair-growing activity using male New Zealand white rabbits weighing 2–3 kg. In Table 1, the groups R$^1$, R$^2$ and A in formula (I) are shown.

TABLE 1

| | |
|---|---|
| R$^1$: | —COONa |
| R$^2$: | —CH(CH$_3$)—CH$_2$—C≡C—CH$_3$ |
| A: | —(CH$_2$)$_3$— |

Each group consisted of 3–4 rabbits. The hair on the back of each rabbit was shaved. The test compound was administered to each rabbit every day for two weeks and the length of the hair newly grown on the shaved back was measured.

More particularly, for subcutaneous administration, the test compound was dissolved in physiological saline to a concentration of 400 μg/ml and 0.25 ml/kg body weight of the solution was administered to each rabbit at one time every day. For oral administration, the test compound was dissolved in distilled water to a concentration of 400 μg/ml and 0.25 ml/kg body weight of the solution was administered to each rabbit at one time every day. After the oral administration, the solution remaining in the oral administration tube was forced into the body with 3 ml of distilled water. As a control, 0.25 ml/kg body weight of physiological saline was subcutaneously administered. Five or more hairs were collected from five regions in the shaved back and the lengths of the hairs were measured. The results are shown in Table 2.

As shown in Table 2, the test compound significantly increased the length of the newly grown hair when compared with the control group.

TABLE 2

| Test Compound | Administration Route | Dose | Length of Hair (mm) |
|---|---|---|---|
| Control | Subcutaneous | 0.25 ml/kg | 2.38 ± 0.07 |
| Beraprost | Subcutaneous | 0.1 mg/kg | 4.54 ± 0.31 |
| | Oral | 0.1 mg/kg | 3.92 ± 0.24 |

We claim:

1. A method of growing hair on an animal, including a human, comprising:

administering to said animal a 5,6,7-trinor-4,8-inter-m-phenylene prostaglandin I$_2$ derivative of the formula (I) below or a pharmaceutically acceptable salt thereof, in an amount effective for stimulating the hair growth of said animal;

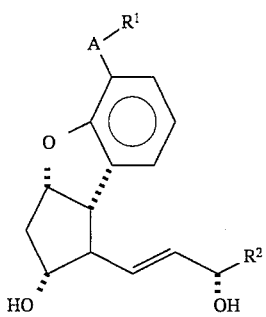

(I)

wherein

R¹ represents hydrogen, a carboxylic group or a functional derivative thereof, —CH₂OH or a pharmaceutically acceptable cation;

A represents
(i) —(CH₂)$_n$—,
(ii) —(CH₂)$_m$—C=CH—(CH₂)$_p$—,
(iii) —(CH₂)$_m$—C≡C—(CH₂)$_p$— or
(iv) —CH₂—O—CH₂— wherein n represents an integer of 0–3, m and p, the same or different, represent 0 or 1;

R² represents
(i) $C_5$–$C_{10}$ straight or branched alkyl group,
(ii) —$C_tH_{2t}$—OR³, wherein t represents an integer of 1–5, R³ represents a $C_1$–$C_5$ straight or branched alkyl group or a phenyl group,
(iii) —$C_tH_{2t}$—CH=C(R⁴)(R⁵)

wherein t has the same meaning as mentioned above, R⁴ and R⁵, the same or different, represent hydrogen, methyl, ethyl, propyl or a butyl group, or
(iv) —$C_tH_{2t}$—C≡C—R⁶ wherein t has the same meaning as mentioned above, R⁶ represents hydrogen, methyl or an ethyl group, and —$C_tH_{2t}$ in (ii), (iii) and (iv) represent a straight or branched alkylene group; and wherein said compound of formula (I) may be in a d-, l- or dl-form.

2. The hair-growing method according to claim 1, wherein said 5,6,7-trinor-4,8-inter-m-phenylene prostaglandin I₂ derivative is represented by formula (II);

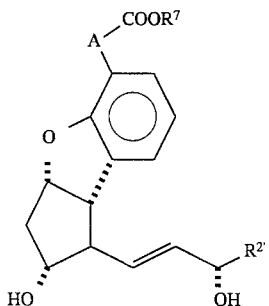

(II)

wherein

R⁷ represents methyl or ethyl, a pharmaceutically acceptable alkaline metal or alkaline earth metal, or an amine or basic amino acid;

A represents
(i) —(CH₂)$_{n'}$—,
(ii) —(CH₂)$_m$—C=CH—(CH₂)$_p$—,
(iii) —(CH₂)$_m$—C≡C—(CH₂)$_p$— or
(iv) —CH₂—O—CH₂— wherein n' represents an integer of 1–3, m and p, have the same meanings as in formula (I);

R²' represents
(i) $C_5$–$C_7$ straight or branched alkyl group,
(ii) —$C_tH_{2t}$—OR³', wherein t represents an integer of 1–3, R³' represents a $C_2$–$C_4$ straight or branched alkyl group or a phenyl group,
(iii) —$C_tH_{2t}$—CH=C(R⁴)(R⁵)

wherein t has the same meaning as mentioned above, R⁴ and R⁵ have the same meanings as in formula (I), or
(iv) —$C_tH_{2t}$—C≡C—R⁶ wherein t has the same meaning as mentioned above, R⁶ has the same meaning as in formula (I), and —$C_tH_{2t}$ in (ii), (iii) and (iv) represent a straight or branched alkylene group; and wherein said compound of the formula (II) may be in a d-, l-or dl-form.

3. The hair-growing method according to claim 2, wherein said alkaline metal and alkaline earth metal for R⁷ is selected from the group consisting of sodium, potassium and calcium, said amine and said basic amino acid for R⁷ are selected from the group consisting of monomethylamine, dimethylamine, trimethylamine, methylpiperidine, monoethanolamine, diethanolamine, triethanolamine and lysine.

4. The hair-growing method according to claim 3, wherein said 5,6,7-trinor-4,8-inter-m-phenylene prostaglandin I₂ derivative is beraprost or a pharmaceutically acceptable salt thereof.

5. The hair-growing method of claim 1, wherein the 5,6,7-trinor-4,8-inter-m-phenylene prostaglandin I₂ derivative of formula (I) is administered orally to said animal.

6. A method for growing hair of an animal, including a human, comprising:

administering to said animal beraprost or a pharmaceutically acceptable salt thereof in an effective amount of 0.01–100 mg per dose thereof, for stimulating hair growth of said animal.

7. The method of claim 6, wherein said effective amount which is administered is 0.01–300 mg/day.

8. The method of claim 6, wherein said animal is a human, and said effective amount which is administered is 0.01 to 300 mg/day.

* * * * *